United States Patent [19]

Shinoda et al.

[11] Patent Number: 5,747,637
[45] Date of Patent: May 5, 1998

[54] BIOABSORBABLE POLYMER AND PROCESS FOR PREPARING THE SAME

[75] Inventors: Hosei Shinoda; Masanobu Ajioka, both of Kanagawa-ken; Kimitaka Chida, Aichi-ken, all of Japan

[73] Assignee: Mitsui Toatsu Chemicals, Inc., Tokyo, Japan

[21] Appl. No.: 697,571

[22] Filed: Aug. 28, 1996

[30] Foreign Application Priority Data

Sep. 7, 1995 [JP] Japan .................................. 7-230366

[51] Int. Cl.$^6$ ...................................................... C08G 63/08
[52] U.S. Cl. ........................... 528/354; 525/408; 525/411; 525/413; 525/415; 525/461; 606/139; 606/154
[58] Field of Search ........................... 528/354; 525/468, 525/411, 413, 415, 461; 606/154, 139

[56] References Cited

U.S. PATENT DOCUMENTS

| | | | |
|---|---|---|---|
| 4,045,418 | 8/1977 | Sinclair | 260/78.3 R |
| 4,605,730 | 8/1986 | Shalaby et al. | |
| 4,857,602 | 8/1989 | Casey et al. | 525/408 |
| 5,252,701 | 10/1993 | Jarrett et al. | |
| 5,320,624 | 6/1994 | Kaplan et al. | 525/411 |
| 5,403,347 | 4/1995 | Roby et al. | 606/230 |
| 5,431,679 | 7/1995 | Bennett et al. | 525/411 |
| 5,442,033 | 8/1995 | Bezwada | 528/354 |
| 5,475,063 | 12/1995 | Kaplan et al. | 525/411 |
| 5,522,841 | 6/1996 | Roby et al. | 525/408 |
| 5,578,046 | 11/1996 | Liu et al. | 606/151 |

FOREIGN PATENT DOCUMENTS

| | | |
|---|---|---|
| 0420541 | 4/1991 | European Pat. Off. |
| 0499204 | 8/1992 | European Pat. Off. |
| 64-56055 | 3/1989 | Japan |

*Primary Examiner*—Duc Truong
*Attorney, Agent, or Firm*—Burns, Doane, Swecker & Mathis, L.L.P.

[57] ABSTRACT

A bioabsorbable, ternary block copolymer consisting essentially of (A) polylactic acid segment, (B) poly($\epsilon$-caprolactone) segment and (C) polyglycolic acid segment, preparation process of the block copolymer, and medical molded articles prepared from said block copolymer. The bioabsorbable block copolymer is excellent in mechanical strength and flexibility and has moderate hydrolyzability and is especially utilized for a surgical monofilament suture.

20 Claims, No Drawings

BIOABSORBABLE POLYMER AND PROCESS FOR PREPARING THE SAME

BACKGROUND OF THE INVENTION

1. Field of the invention

The present invention relates to a bioabsorbable polymer and a process for preparing the same, and a medical article obtained from said bioabsorbable polymer. More specifically, the invention relates to a bioabsorbable polymer which is excellent in mechanical strength such as linear tensile strength and ligation tensile strength and flexibility, and additionally has moderate hydrolyzability, a process for preparing the same, and a medical article obtained from said bioabsorbable polymer.

2. Description of Related Art

Polyesters which are represented by polylactic acid, polyglycolic acid and a lactic acid-glycolic acid copolymer are bioabsorbable polymers and can be nonenzymatically hydrolyzed in a living body. The decomposition products such as lactic acid and glycolic acid are finally converted through a metabolic pathway to carbon dioxide and water, and externally discharged. It has also been known that polymers and copolymers of lactones such as trimethylene carbonate, p-dioxanone and ε-caprolactone are similarly decomposed in a living body, finally converted to carbon dioxide and water and externally discharged.

The preparation process of the above bioabsorbable polymers which has been known is a ring-opening polymerization process, in the presence of a catalyst such as stannous octoate, of glycolide which is a dehydrated cyclic dimer of glycolic acid, lactide which is a dehydrated cyclic dimer of lactic acid, trimethylene carbonate, p-dioxanone and ε-caprolactone, or a mixture of these compounds. Some of these bioabsorbable polymers, for example, polyglycolic acid, polylactic acid and a glycolic acid-lactic acid copolymer have been used for materials of sterilized surgery articles such as sutures and gauze.

However, polyglycolic acid, polylactic acid and a glycolic acid-lactic acid copolymer have high stiffness, and thus it is difficult to make a ligation on stitching up a diseased part after operation, when these polymers are used for the suture in the form of a monofilament. As a result, in order to increase flexibility, many fine monofilaments are usually formed, braided and used as a "so-called" multifilament. However, multifilament-type sutures have a coarse surface and lead to a problem of injuring the surrounding tissue upon stitching. Further, application of a coating agent is required for improving the slip of the filament on making a ligation, and thus the preparation process becomes complex and unfavorable in industry.

In view of the above circumstances, the improvement of the bioabsorbable polymers which are represented by polyglycolic acid, polylactic acid and a glycolic acid-lactic acid copolymer has been tried to increase flexibility. As a result, a lactic acid-hydroxycaproic acid copolymer, a glycolic acid-hydroxycaproic acid copolymer and medical articles formed from these copolymers have been proposed as bioabsorbable copolymers which can be used for surgical sutures in the form of a monofilament.

As to the glycolic acid-hydroxycaproic acid copolymer, for example, U.S. Pat. No. 4,605,730 has disclosed a polymer material which is composed of a sequence on the basis of ε-caprolactone of about 20–35% by weight and glycolide of about 65–80% by weight and has a tensile strength of 30,000 psi or more and a Young's modulus of less than 350,000 psi. The patent has also described sterilized surgical articles comprising the said polymer material and a preparation process of the copolymer which can provide said polymer material. The preparation process of said copolymer which has been described in the patent is a process of forming a low molecular weight prepolymer of ε-caprolactone and glycolide which contains more than 50% by weight of ε-caprolactone and is formed at temperature lower than 220° C.; adding additional glycolide to said prepolymer; polymerizing the mixture which contains the additional glycolide at a temperature higher than 140° C. during a sufficient time for converting to the copolymer at a rate of 80% or more; and providing a copolymer having a crystallinity of 5% or more.

The glycolic acid-hydroxycaproic acid copolymer and the surgery articles formed from said copolymer which have been disclosed in the patent have excellent flexibility and mechanical strength and thus can be advantageously utilized for surgical sutures in the form of a monofilament. However, the filament has a too high hydrolysis rate and is quickly decomposed in a living body. Consequently, the monofilament is unsatisfactory for surgical sutures and the material thereof which are used for a diseased part having a long recovery period.

U.S. Pat. No. 5,252,701 has disclosed a segmented copolymer which has at least two different ester linkages and exhibits bioabsorbability. The patent describes a segmented copolymer comprising fast transesterifying linkages which are substantially composed of glycolate linkages and slow transesterifying linkages which are selected from the group consisting of trimethylene carbonate linkages and caproate linkages. The patent also describes a preparation process of the above segmented copolymer comprising employing sequential addition of at least two different cyclic ester monomers in at least two stages, the first cyclic ester monomer selected from the group consisting of carbonates and lactones, and mixtures thereof, and the second cyclic monomer selected from the group consisting of lactides and mixtures thereof and transesterifying the formed molten copolymer. Said segmented copolymer exhibits properties which markedly differ from the properties of random or block copolymers.

However, as shown in the patent, the segmented copolymer leads to decrease in melting point and crystallinity of the copolymer with a progressing segmentation. Consequently, according to the information of the present inventors, the segmented copolymer exhibits insufficient tensile strength as a monofilament for use in sutures. Also, according to similar information of the present inventors, the segmented copolymer has a too high rate of hydrolysis due to low crystallinity in a living body and is thus unsatisfactory for surgical sutures or the material thereof which is used for the diseased part having a long recovery period.

Further, as to the lactic acid-hydroxycaproic acid copolymer, for example, Japanese Laid-Open Patent SHO 64-56055 has disclosed a biodegradable, medical article comprised of a copolymer having 95–65% by mole of lactic acid units and 5–35% by mole of hydroxycaproic acid units, and a preparation process of the copolymer. The copolymer and medical articles described in the patent have flexibility and can be favorably utilized for the surgical suture in the form of a monofilament. However, the copolymer has low mechanical strength and is too slow in the degradation velocity in the living body, and thus unfavorably remains in the living body for a period longer than needed.

One object of the invention is to overcome the above problems and to provide a bioabsorbable polymer which has excellent mechanical strength and flexibility, additionally has moderate hydrolyzability, and is suited for a material of the surgical monofilament suture, and a process for preparing the bioabsorbable polymer, and a medical article which can be obtained from the bioabsorbable polymer.

SUMMARY OF THE INVENTION

As a result of an intensive investigation in order to overcome the above problems, the present inventors have surprisingly found that the bioabsorbable copolymer which can accomplish the above object can be obtained by previously preparing and isolating polylactic acid having one or more terminal hydroxyl groups, carrying out in a first step the ring-opening polymerization of ε-caprolactone in the presence of the said polylactic acid, adding in a second step glycolide to the reaction system, and carrying out the ring-opening polymerization of glycolide, and that said bioabsorbable copolymer is suited for the raw material of monofilament sutures. Thus the present invention has been completed.

That is, one aspect of the invention is a ternary block copolymer which is obtained by carrying out in a first step the ring-opening polymerization of 20–1200 parts by weight of ε-caprolactone in the presence of 100 parts by weight of polylactic acid having one or more terminal hydroxyl groups and a weight average molecular weight of 2,000–500,000, adding 15–1200 parts by weight of glycolide in a second step in the course of or after completion of the ring-opening polymerization of said ε-caprolactone, and carrying out the ring-opening polymerization of glycolide, and which is comprised of a polylactic acid segment, poly(ε-caprolactone) segment and polyglycolic acid segment, and has a weight average molecular weight of 10,000–1,000,000.

The ternary block copolymer has a molecular weight preferably in the range of 50,000–400,000 in view of the mechanical strength, hydrolysis rate, productivity and processing ability of the ternary block copolymer.

One of the ternary block copolymers which are provided by the invention has the structure represented by formula (1):

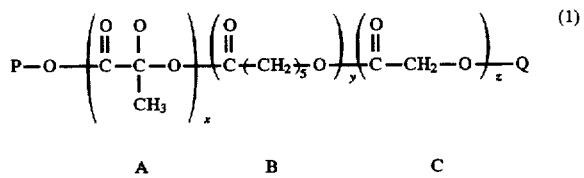

wherein x, y and z are an integer, x:y:z=100:a:b, wherein a is 13–810 and b is 20–1593, P is a hydrogen atom or an alkyl or carboxyalkylene group having 1–18 carbon atoms, and Q is a hydrogen atom or a monovalent or polyvalent metal atom.

Another aspect of the invention is a bioabsorbable, medical article formed from the above ternary block copolymer. A preferred aspect of the bioabsorbable, medical article of the invention includes monofilament suture.

A further aspect of the invention is a process for preparing a ternary block copolymer which is comprised of a polylactic acid segment, poly(ε-caprolactone) segment and polyglycolic acid segment and has a weight average molecular weight of 50,000–1,000,000, comprising carrying out in a first step the ring-opening polymerization of 20–1200 parts by weight of ε-caprolactone in the presence of 100 parts by weight of polylactic acid having one or more terminal hydroxyl groups and a weight average molecular weight of 2,000–500,000, adding 15–1200 parts by weight of glycolide in a second step in the course of or after completion of the ring-opening polymerization of ε-caprolactone, and carrying out the ring-opening polymerization of glycolide.

DETAILED DESCRIPTION OF THE INVENTION

The present invention will hereinafter be illustrated in detail.

The weight average molecular weight (Mw) of polylactic acid, ε-polycaprolactone, polyglycolic acid and copolymer is measured by the method described in the examples below.

The bioabsorbable polymer of the invention is prepared by previously preparing and isolating polylactic acid having a specific molecular weight, mixing the polylactic acid with ε-caprolactone (hereinafter referred to simply as caprolactone), carrying out in first step the ring-opening polymerization of caprolactone in a prescribed amount, successively adding in a second step a prescribed amount of glycolide to the reaction system, and carrying out the ring-opening polymerization of glycolide.

The molecular weight of polylactic acid used in the invention affects mechanical strength and hydrolyzability of the copolymer obtained. That is, when the molecular weight of polylactic acid is too low, copolymer obtained decreases mechanical strength and increases hydrolysis rate.

On the other hand, too high molecular weight of polylactic acid leads to too high melt viscosity of polylactic acid and it becomes difficult to uniformly mix polylactic acid with caprolactone in the caprolactone polymerization in the first step. Thus, polylactic acid which lacks addition of caprolactone or the caprolactone homopolymer generates in an increased amount and the desired ABC-type block copolymer becomes difficult to obtain. As a result, strength, flexibility, hydrolysis rate and other desired properties are liable to be difficult to balance. From the above viewpoint, polylactic acid which can be used has a molecular weight of preferably 2,000–500,000, more preferably 5,000–300,000, most preferably 10,000–150,000.

Polylactic acid above can be prepared by dehydration polycondensation of lactic acid or by ring-opening polymerization of lactide. Both D-lactic acid and L-lactic acid can be used for dehydration polycondensation. For example, when dehydration polycondensation is carried out by using L-lactic acid alone, polylactic acid is influenced by racemization in the course of polymerization and usually contains 80–99.9% by weight of L-lactic acid units and 0.1–20% by weight of D-lactic acid units.

Lactide includes L-lactide which is a cyclic dimer of L-lactic acid, D-lactide which is a cyclic dimer of D-lactic acid, meso-lactide which is formed by cyclic dimerization of D-lactic acid and L-lactic acid, and DL-lactide which is a racemic mixture of L-lactide and D-lactide. Polylactic acid derived from any lactide above can be used for the invention.

The ratio of L-lactic acid unit to D-lactic acid unit in polylactic acid affects crystallinity of copolymer obtained. In view of tensile strength and other mechanical properties, polylactic acid which can be preferably used contains 90–99.9% by weight of L-lactic acid unit and 0.1–10% by weight of D-lactic acid unit.

Polylactic acid which can be used in the invention is terminated with a hydroxyl group. Polylactic acid having the hydroxyl group on one chain end alone can be prepared in the above ring-opening polymerization of lactide by carrying out the polymerization in the presence of an initiator (chain regulator) which includes water, alcohol, hydroxycarboxylic acid and other hydroxyl group containing compounds. Such a polylactic acid can also be prepared by dehydration polycondensation of lactic acid as said above. Polylactic acid having hydroxyl groups on both ends of the polymer chain can be prepared, for example, through the ring-opening polymerization of lactide by using ethylene glycol and other dihydroxyl compounds as the initiator.

It is preferable that polylactic acid prepared by the above method is isolated from the reaction mixture by using well known isolating procedures such as reprecipitation. By said isolating procedures, it is preferable to remove unreacted monomers such as lactide and lactic acid from polylactic acid. The amount of residual unreacted monomers is preferably 10% or less for polylactic acid, more preferably 5% or less and most preferably 3% or less. When it is insufficient to remove the unreacted monomers by the isolating procedures such as reprecipitation, the amount of the residual unreacted monomers can be preferably reduced by purification procedures such as additional reprecipitation, solvent extraction and evacuation procedures under heating.

Polylactic acid used in the invention usually has a molecular weight distribution like common synthetic polymers. The molecular weight distribution is generally shown by the ratio of weight average molecular weight to number average molecular weight (Mw/Mn). For example, polylactic acid prepared by the above dehydration polycondensation process of lactic acid has a relatively broad distribution of molecular weight and Mw/Mn is 2–6. On the other hand, polylactic acid obtained by the ring-opening polymerization process of lactide has Mw/Mn of 1.2–4. In the preparation process of the invention, polylactic acid having a narrow molecular weight distribution can also be used. However, in view of mechanical properties such as strength and flexibility of formed copolymer and decomposition velocity in a living body, prepared polylactic acid has a molecular weight distribution of middle range and thus Mw/Mn is 2 or more to less than 6.

Polylactic acid which can be used for preparing the copolymer of the invention has one or more terminal hydroxyl groups and an weight average molecular weight of 2,000–500,000. Any structure of polylactic acid such as branch-type, comb-type, star polymer-type and dendrimer-type can be approved.

Morphology of polylactic acid used for the raw material is preferably pellet or powder form, more preferably powder form in view of ease in dispersing and mixing polylactic acid and caprolactone.

Polylactic acid used in the invention can contain structural units other than lactic acid units in the range giving substantially no adverse effect on the properties of polylactic acid. No particular restriction is imposed upon the other structural units which can be contained. Units which can be exemplified include a hydroxycaproic acid unit, glycolic acid unit, hydroxybutyrate unit, hydroxyvalerate unit and other hydroxycarboxylic acid units; diol units; and dicarboxylic acid units. The amount of these units depends upon the kind of the structural units contained and is less than 20% by mole in view of giving substantially no adverse effect upon the specific properties of polylactic acid.

It is important to control moisture content of polylactic acid and caprolactone. Because, in the ring-opening polymerization step of caprolactone, the presence of moisture is liable to form a caprolactone homopolymer and results in unfavorable change in properties. The moisture content is preferably 0.1–200 ppm. Caprolactone is dried by using, for example, molecular sieve and moisture is preferably eliminated by additional distillation. Polylactic acid is preferably dried to remove moisture under reduced pressure at room temperature to 120° C.

Moisture content of glycolide influences the molecular weight of copolymer obtained and thus is preferably 1–200 ppm. Moisture of glycolide can be preferably removed by drying under reduced pressure in room temperature to 50° C. or by slugging in a hydrophilic, non-alcoholic organic solvent which does not dissolve glycolide.

Further, lactide, caprolactone, glycolide and other lactones usually contain free hydroxycarboxylic acid such as glycolic acid, hydroxycaproic acid and lactic acid. Free hydroxycarboxylic acid affects molecular weight of copolymer obtained and must be reduced to a minimum content. The minimum content is preferably 10–500 ppm, more preferably 10–200 ppm.

The bioabsorbable polymer of the invention can be prepared by carrying out in the first step the ring-opening polymerization of 20–1200 parts by weight of caprolactone in the presence of 100 parts by weight of above polylactic acid, successively adding in the second step 15–1200 parts by weight of glycolide to the reaction system, and carrying out the ring-opening polymerization of glycolide.

The proportion for use of the above three ingredients is 13–810 parts by mole of hydroxycaproic acid units and 20–1593 parts by mole of glycolic acid units for 100 parts by mole of lactic acid units, when converting to the mole ratio of repeating structural units in the formed copolymer.

The amount of caprolactone particularly influences the flexibility of the copolymer obtained. The flexibility of copolymer obtained is improved with increased amount of caprolactone. The amounts of polylactic acid and glycolide particularly affect mechanical strength of the copolymer obtained. Smaller amounts of polylactic acid and glycolide decrease mechanical strength. On the other hand, larger amounts are liable to improve mechanical strength.

Further, the amounts of polylactic acid, caprolactone and glycolide affect the hydrolysis rate of copolymer obtained. Too high amounts of polylactic acid and caprolactone are liable to cause slow hydrolysis. A larger amount of glycolide is liable to cause too high velocity of hydrolysis.

On the basis of the above viewpoints, the bioabsorbable copolymer having well-balanced mechanical strength, flexibility and hydrolyzability can be obtained by using polylactic acid, caprolactone and glycolide in the above proportion and adding these ingredients to the reaction system through the above procedure and order.

Further, in order to have more preferred tensile strength, flexibility and hydrolyzability at the same time as a bioabsorbable polymer which is suited for preparation of a bioabsorbable monofilament suture, it is more preferred to use polylactic acid, caprolactone and glycolide in the proportions described below;

i) in order to exhibit suitable flexibility of monofilament, the amount for use of caprolactone is 15% or more for the total amount of polylactic acid, caprolactone and glycolide, ii) in order to provide suitable hydrolysis rate for the monofilament, the total amount of polylactic acid and caprolactone is more preferably in the range of 30–90% for the total amount of the three ingredients.

In the invention, other lactones can be used, in addition to the above three ingredients, in combination with caprolactone or glycolide as a monomer of copolymerization. Other lactones include, for example, β-propiolactone, β-butyrolactone, β-valerolactone, δ-valerolactone, p-dioxanone, 3-methyl-1,4-dioxane-2,5-dione and trimethylene carbonate. The amount of these other lactones is preferably 10 parts by weight or less for 100 parts by weight of polylactic acid in view of the object of the invention.

In order to obtain a copolymer having well-balanced strength, flexibility and decomposition velocity, the amount of caprolactone which was used in the first step and remains as an unreacted monomer at the time of glycolide addition in the second step is preferably 10% by weight or less for the amount of glycolide added in the second step. Methods for reducing the unreacted caprolactone in the reaction system immediately before adding glycolide in the second step include, for example, i) a method for increasing the conversion degree of caprolactone by carrying out the caprolactone polymerization in the first step under suitable and sufficient conditions, and ii) a method for removing unreacted caprolactone by heating the reaction system under reduced pressure from the latter half of the first step polymerization or after finishing the first step polymerization until starting the second step polymerization.

The method of i) can enhance the conversion degree to about 99% by suitably controlling a catalyst amount, reaction temperature and reaction time. In order to obtain a copolymer having favorable properties such as mechanical strength and decomposition velocity in the preparation process of the invention, the conversion degree of caprolactone in the first step is preferably raised to 70% or more, more preferably to 80% or more, most preferably to 90% or more.

No particular restriction is imposed upon the procedures for adding glycolide to the reaction system. However, the reaction product obtained by polymerizing caprolactone in the presence of polylactic acid has a high melt viscosity. On the other hand, added glycolide forms a molten liquid of low viscosity in the reaction system. Thus, when a large amount of glycolide is added at a time to the reaction system, good mixture cannot be obtained and the reaction is liable to be non-uniform. The phenomenon inhibits uniform growing of polyglycolic acid segment in the copolymer and renders development of good properties unexpected. Consequently, a preferred procedure for adding glycolide is to continuously or intermittently add a prescribed amount of glycolide by small portions so as to make the amount per minute of glycolide addition 20% or less for the total weight of polylactic acid and caprolactone.

The conversion degree of glycolide affects mechanical strength of the copolymer obtained. Thus, the ring-opening polymerization of glycolide is preferably carrying out until the conversion degree of glycolide attains 95% or more.

The proportion for use of polylactic acid, caprolactone and glycolide, and the procedure and order of addition on these three ingredients affect mechanical strength, flexibility and hydrolyzability of the copolymer obtained. In order to provide the copolymer obtained with excellent mechanical strength and flexibility and moderate hydrolyzability, it is important to add each ingredient to the reaction system according to the above procedure and order.

The ring-opening polymerization processes of caprolactone or glycolide in the presence of polylactic acid include bulk polymerization process, solution polymerization process and dispersion polymerization process. However, in view of contamination of an organic solvent or a dispersant, the bulk polymerization process which can be carried out in a molten state is preferred. The temperature of ring-opening polymerization of caprolactone and glycolide is preferably 130° C. to less than 270° C. Especially the polymerization temperature of caprolactone is preferably higher than the melting temperature of polylactic acid. When polylactic acid is incompletely molten, the polymerization of caprolactone does not often begin from the terminating hydroxyl group and the large amount of caprolactone homopolymer is unfavorably formed as the by-product. On the other hand, too high polymerization temperature leads to decomposition of the formed polymer. From these viewpoints, preferable polymerization temperature of caprolactone is in the range of about 170°–250° C. Similarly preferable polymerization temperature of glycolide is in the range of about 150°–250° C. The ring-opening polymerization is usually carried out in an inert gas atmosphere such as nitrogen.

However, it is important that the ring-opening polymerization of caprolactone is continued without addition of glycolide until the conversion degree of caprolactone attains 70% by weight or more. Such conversion degree can be usually obtained in 0.2–10 hours on the above temperature range. The ring-opening polymerization of glycolide is preferably carried out until the conversion degree of glycolide attains 95% by weight or more. Addition of glycolide is preferably carried out over 0.1–2 hours, more preferably over 0.1–1 hours. Thus, glycolide obtains the conversion ratio of 95% by weight or more. Glycolide is preferably added to the reaction system in a molten state at 100°–150° C.

The conversion degree of caprolactone and glycolide to the copolymer can be analyzed, for example, by dissolving the reaction mixture in hexafluoro-2-propanol, determining residual monomers with a gas chromatograph, and calculating the results.

A polymerization catalyst is preferably used in order to finish any ring-opening polymerization within a short time and to obtain a copolymer having a high molecular weight. Representative catalysts include for example, stannous octoate, tin tetrachloride, zinc chloride, titanium tetrachloride, iron chloride, boron trifluoride ether complex, aluminum chloride, antimony trifluoride, lead oxide and other compounds which primarily contain polyvalent metals. Of these compounds tin compounds, and zinc compounds, are preferably used. Stannous octoate is most preferably used. The amount of polymerization catalyst is preferably 0.001–0.03% by weight for the total amount of raw materials used.

The copolymer obtained by the ring-opening polymerization removes unreacted monomers by heating under reduced pressure in the molten state as such or by cooling, crushing and subsequently heating under reduced pressure. In the case of removing the unreacted monomers in the molten state as such, the reaction mixture is, for example, maintained at 200°–240° C., evacuated over 0.2–1 hour to the final pressure of 13,300 Pa or less, deaerated, and maintained in the intact state for 0.3–2 hours. Evacuation is preferably carried out to the pressure of about 130 Pa.

In the case of removing the unreacted monomers by cooling and crushing the copolymer and subsequently heating under reduced pressure, morphology of the copolymer is preferably powder, pellet or other forms which are as fine as possible. Preferably, the copolymer is maintained at 40°–130° C., evacuated to a pressure of 13,300 Pa or less, deaerated and maintained in the same conditions for 0.5–72 hours. The reduced pressure is desirably about 130 Pa. These methods can be carried out with or without stirring.

The preparation process of the ternary block copolymer in the invention is characterized by previously preparing and isolating polylactic acid having a terminal hydroxyl group and carrying out the ring-opening polymerization of caprolactone in the presence of said polylactic acid. The fact is important for the preparation process of the ternary block copolymer having moderate strength, flexibility and hydrolyzability at the same time. That is, in the process, polylactic acid which has a desired or known structure on molecular weight, molecular weight distribution or optical activity is previously prepared and isolated, and the ternary block copolymer is prepared by using a prescribed amount of the polylactic acid. Consequently, the process of the invention can prepare a block copolymer having a tailor-made structure of the polylactic acid segment which greatly affects the mechanical strength and hydrolyzability.

The ternary block copolymer may be prepared by other processes. For example, lactide is first subjected to ring-opening polymerization to form polylactic acid, caprolactone is subsequently added to the reaction system to form copolymer without isolating polylactic acid from the reaction system, glycolide is added to the resulting copolymer, and the ring-opening polymerization of glycolide is carried out (hereinafter referred to as a continuous three step polymerization process).

However the preparation process of the invention is excellent in the following points as compared with the continuous three step polymerization process. In the continuous three-step polymerization process, the addition of caprolactone in the second step must be carried out at temperature of 200° C. or above because polylactic acid which was formed in the first step must be maintained in a molten state. In such a case, according to the information of present inventors, the polymer/monomer equilibrium between polylactic acid and lactide leads to the presence of residual lactide monomer in an amount of 10% or more at temperature above 200° C. When polylactic acid is contaminated by the lactide monomer, the second segment of the ternary block copolymer becomes a random copolymer segment where lactic acid units contaminate caprolactone units. Such contamination leads to reduction of properties such as decrease in mechanical strength and development of stickiness at room temperature, and is thus unfavorable.

Further, in the continuous three-step polymerization process, caprolactone which is a low viscosity liquid at room temperature is added to molten polylactic acid having high viscosity at high temperature. Thus, mixing and dispersing of these two substances are liable to be non-uniform, growth of the poly(ε-caprolactone) segment from the polylactic acid terminal cannot smoothly progress, contamination of a caprolactone homopolymer increases, and thus properties are unfavorably lowered.

According to the preparation process of the invention, a segment of poly(ε-caprolactone) (hereinafter referred to simply as polycaprolactone) grows in the first step from the terminal hydroxyl group of polylactic acid by carrying out the ring-opening polymerization of caprolactone in the presence of polylactic acid having a terminal hydroxyl group to form a polylactic acid-polycaprolactone AB-type block copolymer. Subsequently, a polymer chain of glycolide (polyglycolic acid segment) grows from the terminal hydroxyl group of the polycaprolactone chain by successive addition of glycolide to the AB-type block copolymer obtained and practice of the ring-opening polymerization of glycolide. Consequently, for example, polylactic acid which has a hydroxyl group on one terminal alone forms an ABC-type ternary block copolymer of polylactic acid (A)-polycaprolactone (B)-polyglycolic acid (C). On the other hand, for example, polylactic acid which has the hydroxyl group on both terminals forms CBABC-type ternary block copolymer.

The molecular weight of bioabsorbable polymer obtained affects mechanical strength and hydrolyzability of the polymer. Consequently, the bioabsorbable polymer of the invention preferably has a molecular weight of 50,000–1,000,000. In the case of using for the surgical suture or bone reinforcement, the molecular weight is usually 50,000–1,000,000, preferably 50,000–400,000.

One of the suitable, bioabsorbable polymers which can be provided by the invention is a ternary block copolymer which comprises 100 parts by mole of lactic acid units, 13–810 parts by mole of hydroxycaproic acid units and 20–1593 parts by mole of glycolic acid units, which includes polylactic acid segment (A), polycaprolactone segment (B) and polyglycolic acid segment (C) on a bonding type of A-B-C represented by formula (1) or C-B-A-B-C, and which has a molecular weight of 50,000–1,000,000;

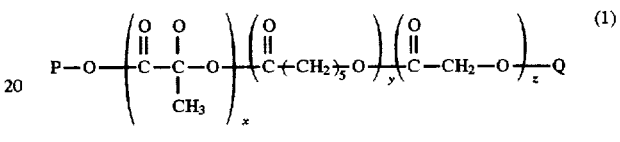

wherein x, y and z are an integer, x:y:z=100:a:b, a is 13–810, b is 20–1593, P is hydrogen atom or an alkyl or carboxyalkylene group having 1–18 carbon atoms, and Q is a hydrogen atom or a monovalent or polyvalent metal atom.

The polymer formed by the preparation process of the invention can contain the above ternary block copolymer and, in addition, a small amount of caprolactone homopolymer, glycolic acid homopolymer, polycaprolactone-polyglycolic acid (BC-type) block copolymer, and a very small amount of polylactic acid, polylactic acid-polycaprolactone (AB-type or BAB-type) block copolymer, and polylactic acid-polyglycolic acid (AC-type or CAC-type) block copolymer.

The amount of these by-product polymers changes depending upon;

i) moisture content of raw materials such as polylactic acid, caprolactone and glycolide and the amount of impurities such as hydroxycarboxylic acid, ii) uniformity of the mixture of polylactic acid and caprolactone in the first step of the reaction, and iii) uniformity of the mixture of the polymer and glycolide at the glycolide addition in the second step of the reaction.

The amount of by-product polymers can be determined by, for example, dissolving and extracting the by-product polymers through Soxhlet extraction from the ternary block copolymer, and dissolving the ternary block copolymer into a good solvent, adding a poor solvent of the ternary block copolymer to the resulting solution, and reprecipitating the ternary block copolymer alone.

The bioabsorbable polymer which was prepared by the above process in the invention can be processed into medical articles by known processes. Medical articles include monofilament suture, bone reinforcing plate, surgical net and slow release medicine.

No particular restriction is imposed upon the preparation process of monofilament suture. Known processes can be applied. For example, a spinning nozzle is mounted on an extruder, and the bioabsorbable polymer of the invention is melt kneaded by the extruder, and a monofilament is formed extruding through the spinning nozzle. Subsequently, the monofilament is oriented by stretching, and the oriented monofilament is annealed and further heat-treated.

Spinning temperature for forming the monofilament is usually higher than the melting point and lower than the decomposition temperature of the copolymer. The temperature is suitably 120°–250° C.

Stretching temperature is usually selected on the basis of glass transition temperature of the monofilament and is preferably 15°–80° C., more preferably 25°–70° C. Draw ratio is preferably 3–20 times, more preferably 3–10 times on the lengthwise direction of the filament. The stretched filament is preferably subjected to annealing and heat-treatment in order to obtain uniformity of properties such as tensile strength, dimensional stability and hydrolzability. Annealing is preferably carried out under relaxation or stretch of 0.5–10% at 40°–130° C. for 0.01–30 seconds.

Heat treatment is preferably carried out after annealing, at 40°–150° C., under reduced pressure of 130–100,000 Pa, for 1–72 hours under tension. The heat-treatment is more preferably carried out at 50°–125° C. under reduced pressure of 130–16,000 Pa, most preferably 130–8,000 Pa.

No particular restriction is imposed upon the size of the monofilament suture in the invention and the diameter is usually 0.05–1 mm, preferably 0.02–0.8 mm. The monofilament suture of the invention is preferably equipped with a sutural needle, when necessary, at least at one end of the monofilament.

In a preferred embodiment of the invention, the surgical monofilament suture of the invention has a linear tensile strength of 200 MPa or more, a ligation tensile strength of 170 MPa or more, and a Young's modulus of 2.1 GPa or less. Hydrolyzability, that is, the residual percentage (proportion for the original value) of linear tensile strength in a living body is 10–90% after progressing for 6 days under conditions described below, 20–80% under more preferred conditions and 30–70% under most preferred conditions. Further, the monofilament suture of the invention has good ligation stability and thus a knot of the ligation does not become loose, when once formed.

The methods for measuring and evaluating these preparations will be fully shown in the examples below.

EXAMPLE

The present invention will hereinafter be illustrated further in detail by way of examples. Below described methods were used for measuring properties in the examples, that is, the molecular weight of polylactic acid and copolymer, conversion degree of ε-caprolactone, glycolide and lactide, composition of copolymer, melting point of copolymer, linear tensile strength, Young's modulus, residual percentage of linear tensile strength after hydrolysis and ligation stability.

1) Molecular weight of polylactic acid and the ternary block copolymer

A solution having concentration of 0.2% by weight was prepared by dissolving polylactic acid in chloroform, or other polymers in hexafluoro-2-propanol (hereinafter referred to as HFP) and the solution was measured by gel permeation chromatograph (hereinafter referred to as GPC) with a model GPC-SYSTEM 21 (manufactured by Showa Denko Co.). The weight average molecular weight (MW) was calculated by using, as a reference, polystyrene in the case of polylactic acid and polymethyl methacrylate in the case of the other polymers.

2) Conversion degree of caprolactone, glycolide and lactide

The formed polymer was dissolved in HFP. The content (amount of the residual monomer) of caprolactone, glycolide and lactide in the polymer was measured by capillary chromatography and the result was calculated.

3) Copolymer composition (part by weight)

An apparatus for measuring nuclear magnetic resonance Model FX-90Q (manufactured by Japan Electron Optical Co.) was used. A mixture of HFP and deuterium chloroform in a volume ratio of HFP:$CDCl_3$=2:1 was used. The range of 1–9 ppm was measured on the $^1H$ nucleus. The ratio of each component (part by weight) in the sample was calculated from each resonance strength of the methyl group (5.2 ppm) on the basis of lactic acid, methylene group (2.4 ppm) on the basis of hydroxycaproic acid, and methylene group (4.8 ppm) on the basis of glycolic acid. The method will hereinafter be referred to as H-NMR analysis.

4) Copolymer melting point (° C.)

A differential scanning calorimeter, Model DSC-8230 (manufactured by RIGAKU Co.) was used.

The melting point was measured by the peak temperature at a temperature increase rate of 10° C./min.

5) Linear tensile strength (MPa) and Young's modulus (GPa)

Measurement was carried out at a chuck width of 40 mm and a speed of testing rate of 100 mm/min by using a tensile tester in accordance with JIS L-1069. Linear tensile strength indicated a maximum load (N) before breakage of the specimen. Young's modulus can be calculated from the slope of the early linear elastic region in the stress-strain curve according to the following equation.

$$\text{Young's modulus} = (\tan\theta \times L \cdot C \cdot S)/(H \times A)$$

where θ is the angle (°) made by the intial straight line portion of the stress/strain curve and the axis of strain (X-axis), L is chuck width (mm), C is chart speed (mm/min), S is load (N/mm) per scale of the axis of stress, H is tensile velocity (mm/min) and A is cross section (mm) of the specimen.

(6) Residual percentage (%) of linear tensile strength after hydrolysis

The specimen (monofilament) was immersed in a phosphate buffer solution at 50° C., pH 7.27 for 6 days. After drying the specimen, linear tensile strength was measured according to the method described in (5) and the percentage for the value before immersion was shown.

(7) Ligation stability

A specimen monofilament was wound two turns so as to adhere on a glass tube having a diameter of 20 mm and a surgeon's knot was applied. Thereafter the specimen was allowed to stand for a prescribed period at 23° C. under the relative humidity of 50%. The time-dependent change on the loosed state of the knot was visually observed. The ligation stability of the specimen was evaluated on the basis of the loosed grade of the knot regarding the ligation of the specimen on the glass tube. Reference of the evaluation was as follows.

Rank A: Specimen was adhered to the tube without looseness on the knot.

Rank B: Specimen was stuck to the tube although looseness was found on the knot.

Rank C: Large looseness was found on the knot and the knot was separated from the glass tube.

Example 1

To a reactor of 1 liter equipped with a mechanical stirrer and vacuum deaerator and dried by heating and evacuation, 100 parts by weight of polylactic acid powder (hereinafter referred to as PLA) having a molecular weight of 86,000, 100 parts by weight of ε-caprolactone (hereinafter referred to as CL) and 0.015% by weight of stannous octoate for the amount of CL, were charged.

Interior of the reactor was maintained at 30° C. under reduced pressure of 130–1300 Pa for about 2 hours while deaerating to remove toluene which was the solvent of stannous octoate. Subsequently, nitrogen was ventilated at 101.000 Pa for about 5 minutes and the reaction mixture as such was heated to 220° C. over 20 minutes and maintained at the temperature for 2 hours. The conversion degree of CL to the copolymer was about 98%.

Next, 100 parts by weight of glycolide (hereinafter referred to as GLD) was melted at 110° C. and continuously charged to the reactor over 10 minutes and violently stirred for 5 minutes. Thereafter, the reaction temperature was raised to 235° C. with slow stirring and maintained at the same level for about 1 hour. The conversion degree of GLD to the copolymer was about 99%. The unreacted residual monomer was removed by gradually reducing the pressure in the reactor. The composition, molecular weight and melting point of the copolymer were measured. Results are illustrated in Table 1.

In the next step, the copolymer thus obtained was melt extruded with an extruder at 240° C. to form a monofilament. The monofilament obtained was stretched at 50° C. to the lengthwise direction at a draw ratio of 7.4 times. Under such tension, the monofilament was annealed at 60° C. for several seconds. Further, the monofilament was heat treated at 110° C. for 3 hours under reduced pressure. The monofilament suture thus obtained had a diameter of 0.2 mm. The linear tensile strength, Young's modulus and residual strength percentage after hydrolysis were measured and evaluated according to the criterion described below. Results are illustrated in Table 2.

① Linear tensile strength
  A: 400 MPa or more
  B: 300 MPa or more–less than 400 MPa
  C: 250 MPa or more–less than 300 MPa
  D: 200 MPa or more–less than 250 MPa
  F: less than 200 MPa ② Young's modulus
  A: 1.3 GPa or less
  B: more than 1.3 GPa–2.1 GPa or less
  C: more than 2.1 GPa–3.0 GPa or less
  F: more than 3.0 GPa ③ Residual strength percentage after hydrolysis
  A: 30% or more–70% or less
  B: 20% or more–less than 30%, or more than 70%–80% or less
  C: 10% or more–less than 20%, or more than 80%–90% or less
  F: less than 10% or more than 90%

Examples 2~9 and Comparative Examples 1~6

The copolymers were prepared by carrying out the same procedures as described in Example 1 except that PLA having a molecular weight shown in Table 1 and Table 3 was used in part by weight shown in Table 1 and Table 3, and that CL and GLD were used in part by weight shown in Table 1 and Table 3. Properties of the copolymer obtained were measured by the same method as described in Example 1 and results are illustrated in Table 1 and Table 3.

Further, the monofilament sutures were prepared by carrying out the same procedures as described in Example 1 except that spinning temperature, stretching temperature, draw ratio and annealing temperature which are shown in Table 2 and Table 4 were employed. Properties of the sutures obtained were measured by the same method as used in Example 1 and results are illustrated in Table 2 and Table 4.

TABLE 1

| | Raw material* (wt. parts) | | | PLA molecular weight | CL conversion degree before GLD addition | Copolymer composition** (wt. parts) | | | | Conversion degree (wt. %) | | Copolymer property | |
|---|---|---|---|---|---|---|---|---|---|---|---|---|---|
| Example | PLA | CL | GLD | (× 10³) | (wt. %) | LA | HCA | GA | CL | GLD | Molecular weight (× 10³) | Melting point (°C.) |
| 1 | 100 | 100 | 100 | 86 | 98 | 100 | 98 | 99 | 98 | 99 | 124 | 60, 173, 228 |
| 2 | 100 | 600 | 300 | 135 | 989 | 100 | 590 | 295 | 98 | 97 | 181 | 60, 169, 225 |
| 3 | 100 | 900 | 300 | 135 | 97 | 100 | 876 | 287 | 98 | 96 | 236 | 62, 165, 222 |
| 4 | 100 | 1200 | 1200 | 16 | 97 | 100 | 1171 | 1163 | 98 | 97 | 138 | 61, 228 |
| 5 | 100 | 100 | 25 | 135 | 96 | 100 | 100 | 25 | 98 | 99 | 133 | 60, 173, 220 |
| 6 | 100 | 20 | 25 | 135 | 98 | 100 | 20 | 24 | 98 | 98 | 102 | 169, 209 |
| 7 | 100 | 1200 | 100 | 360 | 97 | 100 | 1182 | 99 | 99 | 99 | 215 | 63, 180, 220 |
| 8 | 100 | 200 | 800 | 54 | 73 | 100 | 189 | 766 | 95 | 96 | 139 | 205 |
| 9 | 100 | 200 | 500 | 135 | 65 | 100 | 191 | 490 | 96 | 96 | 157 | 187 |

(Note)
*PLA: 1st polymer, CL: 1st monomer, GLD: 2nd monomer
**LA: lactic acid unit, HCA: hydroxycaproic acid unit, GA: glycolic acid unit

TABLE 2

| Example | Spinning Temp. (°C.) | Stretching Temp. (°C.) | Annealing Temp. (°C.) | Draw ratio (times) | Monofilament diameter (mm) | Linear tensile strength (MPa) | | Young's modulus (GPa) | | Residual strength after hydrolysis (%) | | Overall Observations |
|---|---|---|---|---|---|---|---|---|---|---|---|---|
| | | | | | | | Grade | | Grade | | Grade | |
| 1 | 240 | 50 | 60 | 7.4 | 0.2 | 430 | A | 1.4 | B | 62 | A | Excellent |
| 2 | 240 | 55 | 65 | 8.8 | 0.1 | 440 | A | 1.2 | A | 65 | A | Excellent |

TABLE 2-continued

| Example | Spinning Temp. (°C.) | Stretching Temp. (°C.) | Annealing Temp. (°C.) | Draw ratio (times) | Mono-filament diameter (mm) | Linear tensile strength (MPa) | Grade | Young's modulus (GPa) | Grade | Residual strength after hydrolysis (%) | Grade | Overall Observations |
|---|---|---|---|---|---|---|---|---|---|---|---|---|
| 3 | 250 | 55 | 65 | 9.1 | 0.1 | 460 | A | 1.1 | A | 71 | B | Excellent |
| 4 | 240 | 55 | 65 | 8.3 | 0.2 | 470 | A | 1.3 | A | 55 | A | Excellent |
| 5 | 240 | 55 | 65 | 8.3 | 0.2 | 320 | B | 1.2 | A | 79 | B | Excellent |
| 6 | 235 | 55 | 65 | 5.8 | 0.2 | 310 | B | 2.6 | C | 77 | B | good, somewhat hard |
| 7 | 240 | 55 | 65 | 9.1 | 0.1 | 280 | C | 1.1 | A | 88 | C | good, somewhat slow decomposition |
| 8 | 240 | 55 | 65 | 5.6 | 0.2 | 380 | B | 2.2 | C | 19 | C | good, somewhat quick decomposition |
| 9 | 245 | 55 | 65 | 6.4 | 0.2 | 270 | C | 1.6 | B | 14 | C | good, somewhat quick decomposition |

TABLE 3

| Comp. Example | Raw material* (wt. parts) | | | PLA molecular weight (× 10³) | CL conversion degree before GLD addition (wt. %) | Copolymer composition** (wt. parts) | | | | | Conversion degree (wt. %) | Copolymer property | |
|---|---|---|---|---|---|---|---|---|---|---|---|---|---|
| | PLA | CL | GLD | | | LA | HCA | GA | CL | GLD | | Molecular weight (× 10³) | Melting point (°C.) |
| 1 | 0 | 200 | 800 | — | 75 | 100 | 190 | 790 | 95 | 99 | | 141 | 206 |
| 2 | 100 | 100 | 1300 | 86 | 98 | 100 | 99 | 1290 | 98 | 99 | | 155 | 225 |
| 3 | 100 | 600 | 1600 | 135 | 96 | 100 | 580 | 1590 | 97 | 99 | | 192 | 60, 178, 225 |
| 4 | 100 | 1500 | 360 | 87 | 100 | 1400 | 90 | 93 | 90 | | | 208 | 62, 180, |
| 5 | 100 | 0 | 100 | 86 | — | 100 | — | 99 | — | 97 | | 99 | 210 |
| 6 | 100 | 100 | 0 | 135 | 98 | 100 | 99 | — | 99 | — | | 117 | 60, 171, |

(Note)
*PLA: 1st polymer, CL: 1st monomer, GLD: 2nd monomer
**LA: lactic acid unit, HCA: hydroxycaproic acid unit, GA: glycolic acid unit

TABLE 4

| Example | Spinning Temp. (°C.) | Stretching Temp. (°C.) | Annealing Temp. (°C.) | Draw ratio (times) | Mono-filament diameter (mm) | Linear tensile strength (MPa) | Grade | Young's modulus (MPa) | Grade | Residual strength after hydrolysis (%) | Grade | Overall Observations |
|---|---|---|---|---|---|---|---|---|---|---|---|---|
| 1 | 245 | 55 | 65 | 5.8 | 0.2 | 290 | C | 2.2 | C | 0 | F | poor, quick decomposition |
| 2 | 245 | 55 | 65 | 4.8 | 0.2 | 490 | A | 4.2 | F | 0 | F | poor, hard |
| 3 | 245 | 55 | 65 | 5.5 | 0.2 | 380 | B | 3.1 | F | 0 | F | poor, quick decomposition |
| 4 | 245 | 55 | 65 | 9.1 | 0.1 | 240 | D | 1.0 | A | 95 | F | poor slow decomposition |
| 5 | 240 | 55 | 65 | 5.1 | 0.2 | 280 | C | 3.5 | F | 5 | F | poor, hard |
| 6 | 235 | 55 | 65 | 8.3 | 0.2 | 190 | F | 1.2 | A | 92 | F | poor, low strength |

Comparative Example 7

In the presence of 100 parts by weight of PLA powder having MW 86,000, 100 parts by weight of GLD was polymerized by ring opening. The amount of stannous octoate used was 0.015% by weight for the amount of GLD. Polymerization was carried out at 220° C. Viscosity of polymer in the reactor became too high, stirring was difficult, and interior temperature of the reactor exceeded 235° C. Thus, outside temperature of the reactor was set at 235° C. After 1 hour, conversion degree of GLD reached 97% by weight. Although 100 parts by weight of CL was continuously charged to the reactor over about 10 minutes, molten polymer in the reactor did not mix well with CL and the reaction mixture was non-uniform. After 3 hours, an almost uniform mixture was obtained with difficulty. However, the product obtained was dark brown colored and had low melt viscosity. Conversion degree of CL was 89%. Unreacted monomer was removed by gradually reducing the pressure in the reactor.

Molecular weight of PLA, amount of raw materials and sequence of their charge to the reaction system are shown in Table 5. Composition and properties of the copolymer obtained were measured by the same method as Example 1 and results are illustrated in Table 5. The dark brown copolymer obtained was used in an attempt to spin. However, a strange odor was evolved, low viscosity molten liquid alone was discharged from the nozzle, and the filament could not be extruded.

Comparative Example 8

In the presence of 100 parts by weight of PCL pellets having MW 150,000, ring-opening polymerization of 100 parts by weight of LTD was carried out at 220° C. by using 0.015% by weight of stannous octoate for the amount of LTD. After 1 hour, conversion degree of LTD attained about 90% by weight. Polymerization was extended for 2 hours. However, conversion degree of LTD did not increase. Successively, 100 parts by weight of heat melted GLD was continuously charged to the reactor over about 10 minutes and vigorously stirred for about 5 minutes. Thereafter, the reaction temperature was raised to 235° C. under slow stirring and the reaction condition was maintained for an hour. The conversion degree of GLD to the copolymer was about 99% by weight. Unreacted monomer was removed by gradually reducing the pressure of the reactor.

Molecular weight of PCL used, amount of raw materials, and sequence of their charge to the reaction system are shown in Table 5. Composition and properties of the copolymer obtained were measured by the same method as used in Example 1 and results are illustrated in Table 5.

A monofilament suture having a size of 0.2 mm was prepared by carrying out the same procedures as described in Example 1 except that spinning temperature, stretching temperature, draw ratio and annealing temperature were employed as shown in Table 6. Properties of the suture thus obtained were measured by the same method as Example 1 and results are illustrated in Table 6.

Comparative Example 9

In the presence of 100 parts by weight of PCL pellet having MW 150,000, ring-opening polymerization of 100 parts by weight of GLD was carried out at 220° C. in the first step by using 0.015% by weight of stannous octoate for the amount of GLD. Polymerization was initially carried out at 220° C. However, polymer viscosity in the reactor becomes too high, stirring becomes difficult and interior temperature of the reactor exceeded 235° C. Thus external temperature of the reactor was set at 235° C. After 1 hour, conversion degree of GLD attained 98% by weight. Subsequently, 100 parts by weight of LTD was continuously added to the reactor over about 10 minutes. However, the molten polymer in the reactor did not mix well with LTD and remained non-uniform.

After 2 hours, the molten mixture became almost uniform. The molten mixture was extremely dark brown and had low viscosity. Conversion degree of LTD was 86%. Unreacted monomer was removed by gradually decreasing the pressure in the reactor.

Molecular weight of PCL used, amount of raw materials, and sequence of their charge to the reaction system are shown in Table 5. Composition and properties of the copolymer obtained were measured by the same method as described in Example 1 and results are illustrated in Table 5.

A monofilament suture having a size of 0.2 mm was prepared by carrying out the same procedures as described in Example 1 except that spinning temperature, stretching temperature, draw ratio and annealing temperature were employed as shown in Table 6. Properties of the suture thus obtained were measured by the same method as Example 1 and results are illustrated in Table 6.

Comparative Example 10

In the presence of 100 parts by weight of polyglycolic acid pellet (hereinafter referred to as PGA) having Mw 89,000, ring-opening polymerization of 100 parts by weight of CL was tried in the first step by using 0.015% by weight of stannous octoate for the amount of CL. Polymerization was initially carried out at 220° C. However, PGA did not melt and led to a heterogeneous reaction system. The reaction temperature was thus raised to 235° C. After 2 hours, the reaction system increased the viscosity slightly. The reaction mixture obtained by sampling was yellow brown polymer which had non-uniformly dispersed black grains of PGA in several places. Conversion degree of CL was 70%.

Subsequently, 100 parts by weight of LTD was continuously added to the reactor over about 10 minutes. After 4 hours, conversion degree of LTD was 86%. Unreacted monomer was removed by gradually reducing the pressure in the reactor.

Molecular weight of PGA, amount of raw materials and sequence of their charge to the reaction system are illustrated in Table 5. Composition and properties of the copolymer obtained were measured by the same method as Example 1 and results are shown in Table 5.

Dark brown copolymer thus obtained was used in a attempt to spin. However, a strange odor was evolved and low viscosity molten liquid alone was discharged through the nozzle. Thus the filament could not be extruded.

Comparative Example 11

In the presence of 100 parts by weight of PGA having Mw 89,000, ring-opening polymerization of 100 parts by weight of LTD was tried in the first step by using 0.015% by weight of stannous octoate for the amount LTD. The polymerization was initially carried out at 220° C. However, PGA did not melt and led to a heterogeneous reaction system. Thus, the reaction system temperature was raised to 235° C. After 2 hours, viscosity increase was found on the reaction system. The reaction product obtained by sampling was a yellow brown polymer. Conversion of LTD was 85%.

Subsequently, 100 parts by weight of CL was continuously charged to the reactor over about 10 minutes. After 3 hours, conversion degree of CL was 86%. Unreacted monomer was removed by gradually reducing the pressure in the reactor.

Molecular weight of PGA used, amount of raw materials, and sequence of their charge to the reactor are illustrated in Table 5. Composition and properties of the copolymer obtained were measured by the same method as used in Example 1 and results are illustrated in Table 5.

The dark brown copolymer obtained was used in an attempt to spin. However, a strange odor developed and viscosity molten liquid alone was discharged through the nozzle. The filament could not be extruded.

TABLE 5

| Comp. Example | Raw material (wt. parts) | | | 1st polymer M.W. (× 10³) | 1st monomer conversion degree before 2nd monomer addition (%) | Copolymer composition (wt. parts) | | | Conversion (wt. %) | | Copolymer property | |
|---|---|---|---|---|---|---|---|---|---|---|---|---|
| | 1st polymer | 1st monomer | 2nd monomer | | | 1st polymer | 1st monomer | 2nd monomer | 1st monomer | 2nd monomer | M.W. (× 10³) | Melting Point (°C.) |
| 7 | PLA 100 | GLD 100 | CL 100 | 86 | 97 | 100 | 100 | 90 | 98 | 89 | 57 | 60, 179, 207 |
| 8 | PCL 100 | LTD 100 | GLD 100 | 150 | 90 | 100 | 92 | 100 | 91 | 99 | 128 | 61, 170 |
| 9 | PCL 100 | GLD 100 | LTD 100 | 150 | 98 | 100 | 100 | 89 | 99 | 86 | 113 | 60, 181, 224 |
| 10 | PGA 100 | CL 100 | LTD 100 | 89 | 70 | 100 | 72 | 88 | 74 | 87 | 39 | 170 |
| 11 | PGA 100 | LTD 100 | CL 100 | 89 | 85 | 100 | 90 | 85 | 91 | 86 | 45 | 160 |

TABLE 6

| Comp. Example | Spinning Temp. (°C.) | Stretching Temp. (°C.) | Annealing Temp. (°C.) | Draw ratio (times) | Monofilament diameter (mm) | Linear tensile strength (MPa) | Grade | Young's modulus (GPa) | Grade | Residual strength after hydrolysis (%) | Grade | Overall Observations |
|---|---|---|---|---|---|---|---|---|---|---|---|---|
| 8 | 240 | 50 | 60 | 7.3 | 0.3 | 220 | D | 1.2 | A | 5 | F | poor, quick decomposition |
| 9 | 240 | 50 | 60 | 7.4 | 0.2 | 190 | F | 2.2 | C | 11 | C | poor, low strength |

Evaluation of ligation stability

Ligation stability was evaluated on the monofilament sutures obtained in Examples 1–9 by the method described above. Any monofilament maintained the knot steadily for 3 days and was thus classified into Grade A in the evaluation.

The bioabsorbable polymer of the invention had excellent mechanical strength and flexibility. Consequently, a monofilament suture and other medical molded articles having excellent mechanical strength and flexibility can be prepared from the bioabsorbable polymer. The monofilament suture obtained from the bioabsorbable polymer of the invention has residual tensile strength of 10–90% after immersion at 50° C. for 6 days in a phosphate buffer solution having pH 7.27. Thus, the suture has suitable hydrolyzability and, further, is excellent in ligation stability. Consequently, the monofilament suture formed from the bioabsorbable polymer of the invention is particularly useful for the suture of surgery which requires a week to 10 days for the period from operation to suture removal.

The bioabsorbable polymer having such characteristics can be obtained only by employing the process of the invention. Thus, the process of the invention is extremely useful as a process for preparing the raw material polymer of medical molded articles.

What is claimed is:

1. A ternary block copolymer having a weight average molecular weight of 10,000–1,000,000 and consisting essentially of a polylactic acid segment, poly(ε-caprolactone) segment and polyglycolic acid segment, and being prepared by carrying out ring-opening polymerization of 20–1200 parts by weight of ε-caprolactone in the presence of 100 parts by weight of polylactic acid having one or more terminal hydroxyl groups and a weight average molecular weight of 2,000–500,000, in a first step, and carrying out in a second step addition and ring-opening polymerization of 15–1200 parts by weight of glycolide in the course of or after completion of the ring-opening polymerization of ε-caprolactone.

2. The ternary block copolymer according to claim 1 wherein 20–300 parts by weight of ε-caprolactone and 225–1200 parts by weight of glycolide are used for 100 parts by weight of polylactic acid.

3. The ternary block copolymer according to claim 1 wherein the weight average molecular weight of the ternary block copolymer is 50,000–400,000.

4. The ternary block copolymer according to claim 3 wherein the amount of ε-caprolactone is 15% or more for the total amount of polylactic acid, ε-caprolactone and glycolide and the total amount of polylactic acid and ε-caprolactone is in the range of 30–90% for the total of polylactic acid, ε-caprolactone and glycolide.

5. An ABC type ternary block copolymer consisting essentially of a polylactic acid segment (A), polycaprolactone segment (B), and polyglycolic acid segment (C) and being represented by the formula (1):

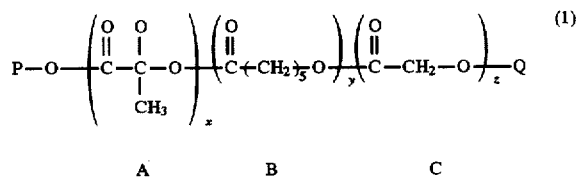

wherein x, y and z are an integer, x:y:z=100: a:b, a is 13–810, b is 20–1593, P is hydrogen atom or an alkyl or carboxyalkylene group having 1–18 carbon atoms, and Q is a hydrogen atom or a monovalent or polyvalent metal atom.

6. A process for preparing a ternary block copolymer having a weight average molecular weight of 10,000–1,000, 000 and consisting essentially of a polylactic acid segment, poly(ε-caprolactone) segment and polyglycolic acid segment, and being prepared by carrying out ring-opening polymerization of 20–1200 parts by weight of ε-caprolactone in the presence of 100 parts by weight of polylactic acid having one or more terminal hydroxyl groups and a weight average molecular weight of 2,000–500,000, in a first step, and carrying out in a second step addition and ring-opening polymerization of 15–1200 parts by weight of glycolide in the course of or after completion of the ring-opening polymerization of ε-caprolactone.

7. The process for preparing of the ternary block copolymer according to claim 6 wherein 20–300 parts by weight of ε-caprolactone and 25–1200 parts by weight of glycolide are used for 100 parts by weight of polylactic acid.

8. The process for preparing ternary block copolymer according to claim 6 wherein the amount of ε-caprolactone is 15% or more for the total amount of polylactic acid, ε-caprolactone and glycolide and the total amount of polylactic acid and ε-caprolactone is in the range of 30–90% for the total of polylactic acid, ε-caprolactone and glycolide.

9. The process for preparing the ternary block copolymer according to claim 8 wherein addition of glycolide is initiated at the time when the conversion degree of ε-caprolactone attains 70% by weight or more.

10. The process for preparing the ternary block copolymer according to claim 9 wherein glycolide is continuously or intermittently added so as to make the amount per minute of the glycolide addition 20% or less for the total amount of polylactic acid and ε-caprolactone.

11. A bioabsorbable medical article prepared from the ternary block copolymer according to claim 1.

12. A bioabsorbable medical article prepared from the ternary block copolymer according to claim 2.

13. A bioabsorbable medical article prepared from the ternary block copolymer according to claim 3.

14. A bioabsorbable medical article prepared from the ternary block copolymer according to claim 4.

15. A bioabsorbable medical article prepared from the ternary block copolymer according to claim 5.

16. The bioabsorbable medical article according to claim 11 wherein the bioabsorbable medical article is a monofilament suture.

17. The bioabsorbable medical article according to claim 12 wherein the bioabsorbable medical article is a monofilament suture.

18. The bioabsorbable medical article according to claim 13 wherein the bioabsorbable medical article is a monofilament suture.

19. The bioabsorbable medical article according to claim 14 wherein the bioabsorbable medical article is a monofilament suture.

20. The bioabsorbable medical article according to claim 15 wherein the bioabsorbable medical article is a monofilament suture.

* * * * *